(12) United States Patent
Thakore

(10) Patent No.: US 11,754,650 B2
(45) Date of Patent: Sep. 12, 2023

(54) MRI SHIELD

(71) Applicant: Howmedica Osteonics Corp., Mahwah, NJ (US)

(72) Inventor: Mayur J. Thakore, Parsippany, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 34 days.

(21) Appl. No.: 17/225,632

(22) Filed: Apr. 8, 2021

(65) Prior Publication Data

US 2021/0318400 A1   Oct. 14, 2021

Related U.S. Application Data

(60) Provisional application No. 63/008,142, filed on Apr. 10, 2020.

(51) Int. Cl.
    *G01R 33/422* (2006.01)
    *A61B 5/055* (2006.01)

(52) U.S. Cl.
    CPC ............ *G01R 33/422* (2013.01); *A61B 5/055* (2013.01)

(58) Field of Classification Search
    CPC .............................. G01R 33/422; A61B 5/055
    See application file for complete search history.

(56) References Cited

U.S. PATENT DOCUMENTS

| | | | |
|---|---|---|---|
| 8,514,043 B2* | 8/2013 | Wang | G01R 33/421 335/301 |
| 8,878,532 B2 | 11/2014 | Doerr et al. | |
| 9,402,996 B2 | 8/2016 | Tran et al. | |
| 10,813,564 B2* | 10/2020 | Rosen | A61B 5/398 |
| 2005/0113676 A1 | 5/2005 | Weiner et al. | |
| 2008/0023010 A1 | 1/2008 | Inman et al. | |
| 2015/0005616 A1* | 1/2015 | Saha | A61B 6/4417 324/322 |
| 2016/0069968 A1* | 3/2016 | Rothberg | G01R 33/38 324/322 |
| 2016/0281933 A1* | 9/2016 | Ham | G01R 33/3802 |
| 2017/0290207 A1* | 10/2017 | Smith | H05K 9/0024 |
| 2018/0137971 A1* | 5/2018 | Jang | H01F 38/14 |
| 2018/0198186 A1* | 7/2018 | Hwang | H01F 38/14 |
| 2018/0198305 A1* | 7/2018 | Hwang | H05K 9/0075 |
| 2018/0271372 A1* | 9/2018 | Lee | A61B 5/0035 |
| 2018/0315527 A1* | 11/2018 | Lee | H01F 38/14 |
| 2018/0335491 A1* | 11/2018 | Yang | G01R 33/3657 |

(Continued)

*Primary Examiner* — Dixomara Vargas
(74) *Attorney, Agent, or Firm* — Lerner David LLP

(57) ABSTRACT

A multi-layered shielding apparatus for reducing the heating of an implanted device within a patient during an MRI scan is disclosed. The shield comprises four internal layers circumferentially surrounded by a waterproof fabric pouch for maintaining composure of the shield and providing a comfortable interface for the patient. The second layer is a thin high conductive energy permeable layer for absorbing a substantial amount of RF energy. The first and third layers are thick low conductive energy absorbent layers that surround the second layer to absorb the RF currents produced by the interaction between the RF energy and the high conductive layer. The fourth layer is a nonconductive polymer layer for insulating the human tissue from any RF currents produced among the other layers.

21 Claims, 1 Drawing Sheet

(56) References Cited

U.S. PATENT DOCUMENTS

| | | | | |
|---|---|---|---|---|
| 2019/0148988 A1* | 5/2019 | Hwang | ............... | H02J 50/20 |
| | | | | 307/104 |
| 2020/0147412 A1* | 5/2020 | Ni | ............... | G01R 33/3403 |
| 2020/0246637 A1* | 8/2020 | Wang | ............... | A61N 5/1049 |
| 2021/0162236 A1* | 6/2021 | Shvartsman | ............... | A61B 5/055 |
| 2021/0325482 A1* | 10/2021 | Setegn | ............... | A61B 5/242 |
| 2022/0193450 A1* | 6/2022 | Yu | ............... | A61N 5/1039 |

* cited by examiner

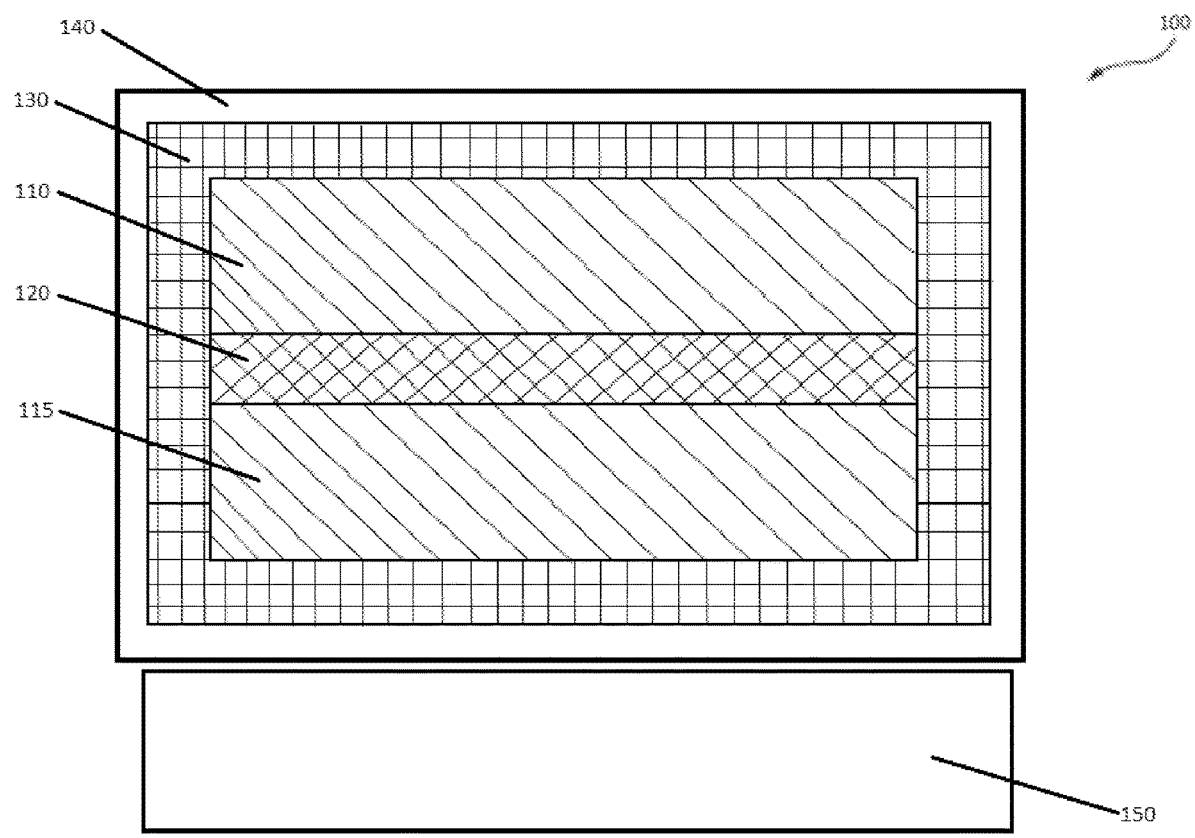

MRI SHIELD

CROSS REFERENCE TO RELATED APPLICATIONS

The present application claims the benefit of the filing date of U.S. Provisional Patent Application No. 63/008,142 filed Apr. 10, 2020, the disclosure of which is hereby incorporated by reference.

BACKGROUND OF THE INVENTION

Magnetic resonance imaging (MRI) is a valuable technique for diagnosis of a broad range of pathological conditions in all parts of the body. MRI uses radiofrequency (RF) waves and a strong magnetic field to provide clear and detailed pictures of internal organs and tissues. Although MRI has great utility on the average patient, many patients have implants which are made entirely or partially from a metallic material that may be magnetic or paramagnetic, such as cardiac assist devices, insulin pumps, guided catheters, orthopedic implants, etc.

The use of MRI with patients who have implanted or non-implanted medical assist devices can present a problem during examination. Conductive elements exposed to RF energy can produce electrical currents, called RF currents. When conductive materials are exposed to the gradient magnetic field, they may interact with RF energy, leading to the formation of RF currents within the conductive material. RF currents produced within the conductive material can cause intense heating along the conductive element and, consequently, also at adjacent tissue. Even if an MRI scan is conducted on an area of the body remote from the device, the design of the MRI system creates high levels of RF energy that are still directed to the implant and may cause the device and surrounding tissue to warm up. Consequently, discomfort and thermal damage to the surrounding tissue may ensue.

In addition to heating, electrical interference of implanted medical devices can damage the circuitry of the device's systems or interfere with the operation or functionality of the device. Since the sensing systems and conductive elements of these medical devices are responsive to changes in local electromagnetic fields, the medical devices are vulnerable to external sources of severe electromagnetic noise, and in particular, electromagnetic fields emitted during imaging. Many devices include sensing and logic systems that respond to low-level electrical signals emanating from the monitored tissue region of the patient, and these devices may include metal wire leads which can act as antennae and provide a path for the induced energy to travel to and possibly damage circuitry.

Due to the high sensitivity of the devices under imaging, patients with these devices require maximum protection from the RF waves created by an MRI scanner to avoid mishaps. One technique for shielding RF waves entails shielding the entire body, which would preclude effective imaging using an MRI scanner. Other known techniques include localized shielding. However, current shielding products do not sufficiently attenuate radiofrequency waves and electromagnetic fields while also dissipating heat.

Thus, a new and unique design is needed to improve upon the aforementioned shortcomings.

BRIEF SUMMARY OF THE INVENTION

The present disclosure describes an MRI shield that provides an enhanced barricade to radiofrequency (RF) waves in a localized area, while still permitting the normal flow of RF waves to uncovered areas surrounding the shield to allow for clear imaging results.

In one aspect of the present disclosure, an MRI shield includes a plurality of protective layers comprising a variety of conductive and nonconductive materials. The conductive materials and the layers thereof may have varying conductivity. For example, a high conductive layer may be made from a magnetic or paramagnetic material, such as titanium, cobalt-chromium, stainless steel, molybdenum, tantalum, niobium and the like, and a low conductive layer may be made from a liquid or gel substance, such as an aqueous saline gel, polyacrylic acid or bovine serum. Nonconductive layers can be made from dielectric materials such as ceramics and polymers, such as polyvinyl chloride (PVC) or ultra-high-molecular-weight polyethylene (UHMWPE). These conductive and nonconductive layers may be wrapped in a nonflammable waterproof fabric pouch to be placed on a localized area of the patient. In one embodiment of the disclosure, the MRI shield includes a layer of a high conductive energy permeable shield, two individual layers of a low conductive energy absorbent shield sandwiching the high conductive energy permeable shield, an enclosed nonconductive plastic or polymer shield wrapped around all dimensions of the unit formed by the above mentioned layers, and a water proof fabric pouch containing the entire structure. The layers may have differing thicknesses. For example, the high conductive layer may be thinner than the low conductive layers. Such layers operate together to shield RF energy, absorb RF energy, and dissipate heat generated by the RF energy. In this regard, RF currents within the implantable device are minimized so that localized heating of an implanted device is negligible in terms of its effect on surrounding tissue and on the device itself.

In certain preferred embodiments, a multi-layered shielding apparatus for interrupting a radio frequency electromagnetic field may comprise a first layer comprising a low conductive material, a second layer adjacent the first layer comprising a high conductive material, a third layer adjacent the second layer comprising the low conductive material of the first layer, and a fourth layer adjacent the third layer comprising a nonconductive material. The first, second and third layers may be arrange sequentially in a single stack. The shield may comprise a waterproof fabric circumferentially surrounding the first, second, third and fourth layers. The first and third layers may include a saline solution. The saline solution may comprise 5% salt. The saline solution may be in the form of a gel. The high conductive material may be a planar mesh made from one of titanium, stainless steel, cobalt-chromium, tantalum, molybdenum or niobium. The fourth layer may be a distal portion of a nonconductive shell made form a polymer sheet configured to circumferentially wrap around the first, second and third layers, the nonconductive shell also having a proximal portion disposed adjacent the first layer such that the first layer is positioned between the proximal portion and the second layer. The fourth layer may comprise polyvinyl chloride (PVC). The fourth layer may comprise ultra-high-molecular-weight-polyethylene (UHMWPE). The fourth layer may be continuous without interruption. The first layer may have a thickness between 5-7 millimeters. The second layer may have a thickness between 2-3 millimeters. The third layer may have a thickness between 5-7 millimeters. The fourth layer may have a thickness between 2-4 millimeters. The first and third layers may comprise synovial fluid.

In certain alternative embodiments, a shield for shielding energy produced by an MRI machine may comprise a first layer comprised of a first material, a second layer comprised of a second material, a third layer comprised of a third material, a shell comprised of a fourth material and surrounding the first, second and third layers, and a pouch containing the shell and the layers, wherein the first and third materials have a conductivity lower than the second material and the fourth material is nonconductive. The second material may be a metal mesh material. The first and third materials may be the same and may be a saline solution. The fourth material may be a sheet of PVC or UHMWPE.

BRIEF DESCRIPTION OF THE DRAWINGS

The FIGURE is a schematic cross-sectional view of an MRI shield as it would be placed adjacent the targeted anatomy of the patient to shield an implanted device.

DETAILED DESCRIPTION

The present disclosure will now be described more fully hereinafter with reference to the accompanying drawings, in which some, but not all aspects of the disclosure are shown. Indeed, the disclosure may be embodied in many different forms and should not be construed as being limited to the aspects set forth herein. Like numbers refer to like elements throughout.

As used herein, the term "proximal," when used in connection with a shield or components of the shield, refers to the end of the shield closer to a magnetic resonance imaging (MRI) device and farther from the patient's anatomy when the shield is being used as intended. On the other hand, the term "distal," when used in connection with the shield or components of the shield, refers to the end of the shield farther away from the MRI device and closer to the patient's anatomy when the shield is being used as intended. As used herein, the terms "substantially," "generally," "approximately," and "about" are intended to mean that slight deviations from absolute are included within the scope of the term so modified.

The MRI shield described in the present disclosure is designed to optimize the prevention of radiofrequency (RF) energy produced by an MRI device from reaching a localized area on a patient being imaged, such as a patient having an implant made of a conductive material, such as a magnetic or paramagnetic material.

The preferred embodiment of a shield 100 is illustrated in the FIGURE, wherein each layer is distinguished by a different pattern and like patterns represent like composition. The MRI device is not shown in the FIGURE, but will be located on a side of shield 100 opposing human tissue 150 such that shield 100 acts as a barrier between the MRI device and human tissue 150. The layers of shield 100 will be described from the proximal end to the distal end, i.e., in the same order in which RF waves will travel toward human tissue 150.

The first and most proximal layer that will receive RF waves is waterproof fabric 140. Waterproof fabric 140 is a pouch that wraps around each of the other layers to maintain the structure and composition of shield 100. Because waterproof fabric 140 is circumferentially wrapped around all other layers, it is also the last and most distal layer that provides comfort to the patient when shield 100, which may bear a substantial weight, is placed on top of or adjacent to the patient. Waterproof fabric 140 is waterproof for the preservation of shield 100 and each of shield's internal layers to prevent wear or decomposition during the course of its use. However, in some embodiments, fabric 140 may not be waterproof. Waterproof fabric 140 can be made of vinyl, nylon, cotton, and the like and may comprise one or more woven or nonwoven layers.

The next layer immediately distal to waterproof fabric 140 is a proximal portion of a nonconductive shell 130. Nonconductive shell 130 is similar to waterproof fabric in that it wraps around and completely envelops the layers contained within it to deter leakage of RF current from any direction. Nonconductive shell 130 will be discussed below in further detail.

The next layer immediately distal to nonconductive shell 130 is a proximal low conductive energy absorbent (LCEA) layer 110. Proximal LCEA layer 110 includes a saline solution which comprises approximately 5% NaCl and may be in the form of a liquid or a gel. However, in other embodiments, the salt content can be between 5% and 15%. Other salts are also contemplated for use. Also, other low conductive compositions may be used in the LCEA layer, such as a biological fluid, e.g., bovine serum or synovial fluid. LCEA layer 110 may further include polyacrylic acid (PAA) to sustain a desired degree of electric conductivity. The saline solution may be contained in a flexible bag, such as a bag made out of PVC or a phthalate such as Di(2-ethylhexyl)phthalate (DEHP). Thus, while the FIGURE does not show the bag as a separate layer, it should be understood that proximal LCEA layer 110 is inclusive of such a bag. Proximal LCEA layer 110 absorbs a substantial portion of energy produced in the form of RF currents by a distally adjacent high conductive energy permeable (HCEP) layer 120, as will be discussed below. Although proximal LCEA layer 110 includes a low conductive substance, the nature of its conductivity will cause it to absorb a portion of the RF energy before the energy reaches HCEP layer 120, even if such portion of the energy absorbed is relatively small compared to HCEP layer 120. Thus, absorption of RF energy by proximal LCEA layer 100 reduces the energy absorption burden on HCEP layer 120. In the illustrated embodiment, proximal LCEA layer 110 is thicker relative to other layers to absorb and disperse both electrical currents and thermal energy produced by HCEP layer 120, as discussed further below. The preferred thickness of proximal LCEA layer 110 is between approximately 5-7 millimeters. Thickness is defined as the proximal-distal dimension of a particular layer. LCEA layer 110 is functional at other thicknesses. However, thicknesses thinner than 5 millimeters do not absorb as much RF energy and current while thicknesses thicker than 7 millimeters have a tendency to become needlessly bulky or cause undesirable crimping throughout the layer which may potentially reduce the effectiveness of the shielding.

The next layer immediately distal to proximal LCEA layer 110 is HCEP layer 120. HCEP layer 120 is thinner relative to all other layers and composed of a conductive metal mesh in planar form. The metal is preferably titanium for its paramagnetic qualities and ability to release energy. However, other materials may be used, such as stainless steel, cobalt-chromium, molybdenum, and tantalum, for example. HCEP layer 120 is used to absorb maximum electromagnetic energy to cut off a substantial amount of RF waves from reaching human tissue 150. When RF energy interacts with conductive material, electric currents called RF currents are produced within the material. The flow of RF currents causes the generation of heat. The currents produced within HCEP layer 120 generate heat which is transmitted to and dissipated among surrounding layers, primarily the LCEA layers, to allow HCEP layer 120 to continue optimally absorbing RF energy without overheating. The preferred thickness of HCEP layer 120 is between approximately 2-3 millimeters, however thinner or thicker thicknesses are possible. It is also contemplated that HCEP layer 120 comprises a metal, nonporous sheet in addition to or in place of a planar metal mesh.

The next layer immediately distal to HCEP layer 120 is a distal LCEA layer 115 substantially the same as proximal LCEA layer 110 described above. However, in some embodiments, distal LCEA 115 may be made of a different material than proximal LCEA 110 but, nonetheless, still have a low conductivity relative to HCEP layer 120. Distal LCEA layer 115 provides substantially the same function as proximal LCEA layer 110, e.g., absorb and dissipate the RF currents produced by HCEP layer 120 and prevent excessive heat from travelling toward human tissue. Surrounding HCEP layer 120 with two LCEA layers 110, 115 transmits energy away from HCEP layer 120 to allow HCEP layer 120 to continuously absorb RF energy reaching shield 100. Distal LCEA layer 115 further contributes to the absorption of residual RF energy that may penetrate and/or bypass HCEP layer 120. The preferred thickness of distal LCEA layer 115 is between approximately 5-7 millimeters. In this regard, distal LCEA layer 115 is preferably the same thickness as proximal LCEA layer 110. However, in some embodiments, distal LCEA 115 layer may be thicker or thinner than proximal LCEA 110. Regardless, LCEA layers 110, 115 are preferably thicker than HCEP layer 150.

The next layer immediately distal to distal LCEA layer 115 is a distal portion of nonconductive shell 130. In the illustrated embodiment, nonconductive shell 130 comprises a polymer sheet that is wrapped about LCEA and HCEP layers. In particular, nonconductive shell 130 may be composed of polyvinyl chloride (PVC) or ultra-high-molecular-weight polyethylene (UHMWPE). In addition, nonconductive shell 130 is a uniform and continuous sheet such that it does not have any gaps or pores around its surface area. In other words, nonconductive shell 130 is continuous around its surface without interruption and will insulate all other layers contained within it like a sealed bag. Nonconductive shell 130 acts as an electric insulator by preventing most or all of the remaining RF current from traveling to the distal-most portion of waterproof fabric 140 positioned adjacent human tissue 150. In this regard, shell 130 is wrapped about LCEA and HCEP layers to prevent RF current leakage from any direction. However, it is contemplated that in some embodiments, shell 130 may not be a shell 130 but rather separate layers such that the shield has a proximal and distal nonconductive layers or just a distal layer. Other dielectric materials are contemplated but not advisable as it will make the shield rigid and less mendable, such as ceramics, for example. However, polymer is preferable at least because it has more flexibility so that MRI shield 100 can conform to the patient's anatomy during use. The preferred thickness of nonconductive shell 130 is between approximately 2-4 millimeters, however other thicknesses are contemplated.

Finally, the last and distal-most layer that is distal to nonconductive shell 130 and adjacent to human tissue 150 is waterproof fabric 140 as described above. Waterproof fabric 140 further insulates human tissue 150 from any heat generated within internal layers of shield 100 and acts as a comfortable interface between shield 100 and human tissue 150.

Viewing fully assembled shield 100 holistically when in use during an MRI scan, proximal LCEA layer 110, HCEP layer 120 and distal LCEA layer 115 are arranged sequentially in a single stack, the stack contained within nonconductive shell 130 which is contained within waterproof fabric 140. The RF energy produced by the MRI device will be substantially absorbed by HCEP layer 120. The interaction between the RF energy and HCEP layer 120 will excite RF currents within HCEP layer 120 that generate heat. RF currents, along with heat generated in HCEP layer 120, will be absorbed by surrounding proximal LCEA layer 110 and distal LCEA layer 115. Any remaining RF energy that is not absorbed by HCEP layer 120 and surrounding LCEA layers 110 and 115 may be shielded by nonconductive shell 130 in all surrounding dimensions. Nonconductive shell 130 will act as an insulator and block RF current transmitting toward human tissue 150. Reduction in the transmission of RF current causes a reduction in heat magnitude.

In use, shield 100 is placed on top of or adjacent human tissue 150 to cover the anatomy of the patient where an implantable or conductive device may be located. Since MRI machines typically emit energy 360 degrees about the patient, shield 100 may be wrapped about a patient's limb, torso, or other anatomy so as to shield the implanted device from all possible angles. In this regard, it is contemplated that shield 100 may be constructed in various sizes employing the same multi-layered design as described above. For example, shield 100 may be sized to cover the entire torso of a patient, the entire lower half of a patient's body, the head or face, or a relatively smaller patch of the patient's body such as a portion of the chest (e.g., to cover the heart), arm or leg. Further, shield 100 may be constructed to circumferentially wrap around an appendage of the patient.

Example

In a simulated use, a prosthetic device was exposed to a magnetic resonance ("MR") field in accordance with ASTM F2182-19. The prosthetic device in this simulation was a femoral hip prosthesis embedded in a lower torso phantom. The lower torso phantom was designed based on the dimension of a lower torso of a human body and included a saline gel inside a dielectric shell in the shape a lower human torso with two legs. The hip prosthesis was embedded in one of the legs to simulate an implanted hip prosthesis. The hip prosthesis and lower torso phantom were exposed to a 1.5 T MR environment with and without shield 100. Shield 100 was sized and shaped to wrap around the leg with the prosthesis. Since the electromagnetic energy inside the leg phantom differs between the two test cases (i.e., with and without shield 100) due to shield 100 reflecting and absorbing electromagnetic fields, a reference titanium rod and predetermined whole body Specific Absorption Rate ("SAR) were used to normalize measured temperatures in order to examine temperature differences between the test cases.

After being normalized to a whole body SAR of 2 Watts/kilogram, the RF-induced heating on or near the prosthetic device was reduced from 4.20 degrees Celsius without the shield to 2.90 degrees Celsius with the shield, demonstrating a 31% reduction in RF heating. It was also determined that an optimum thickness of the low conductive energy absorbent (LCEA) shielding after filling 5% saline solution is about 5 millimeters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A shielding apparatus comprising:
   a first layer positioned on a first plane comprising a low conductive material;
   a second layer positioned on a second plane parallel to the first plane and adjacent the first layer, the second layer comprising a high conductive material;
   a third layer positioned on a third plane parallel to the second plane and adjacent the second layer, the third layer comprising the low conductive material of the first layer; and
   a fourth layer surrounding the first, second and third layers, the fourth layer comprising a nonconductive material,
   wherein the shielding apparatus is configured for interrupting a radiofrequency electromagnetic field of an MRI machine.

2. The shielding apparatus of claim 1, wherein the first, second and third layers are arranged sequentially in a single stack.

3. The shielding apparatus of claim 1, further comprising a waterproof fabric circumferentially surrounding the first, second, third and fourth layers.

4. The shielding apparatus of claim 1, wherein the first and third layers include a saline solution.

5. The shielding apparatus of claim 4, wherein the saline solution comprises 5% salt.

6. The shielding apparatus of claim 4, wherein the saline solution is in the form of a gel.

7. The shielding apparatus of claim 1, wherein the high conductive material is a planar mesh made from one of titanium, stainless steel, cobalt-chromium, tantalum, molybdenum and niobium.

8. The shielding apparatus of claim 1, wherein the fourth layer is made from a polymer sheet.

9. The shielding apparatus of claim 1, wherein the fourth layer comprises polyvinyl chloride (PVC).

10. The shielding apparatus of claim 1, wherein the fourth layer comprises ultra-high-molecular-weight polyethylene (UHMWPE).

11. The shielding apparatus of claim 1, wherein the fourth layer is continuous without interruption.

12. The shielding apparatus of claim 1, wherein the first layer has a thickness between 5-7 millimeters.

13. The shielding apparatus of claim 1, wherein the second layer has a thickness between 2-3 millimeters.

14. The shielding apparatus of claim 1, wherein the third layer has a thickness between 5-7 millimeters.

15. The shielding apparatus of claim 1, wherein the fourth layer has a thickness between 2-4 millimeters.

16. The shielding apparatus of claim 1, wherein the first and third layers comprise synovial fluid.

17. A shield, comprising:
   a first layer comprised of a first material;
   a second layer comprised of a second material;
   a third layer comprised of a third material;
   a shell comprised of a fourth material and surrounding the first, second, and third layers; and
   a pouch containing the shell and the layers,
   wherein the first and third materials have a conductivity lower than the second material and the fourth material is nonconductive,
   wherein the first, second and third layers are each disposed on separate parallel planes, and
   wherein the shield is configured to shield energy produced by an MRI machine.

18. The shield of claim 17, wherein the second material is a metal mesh material.

19. The shield of claim 17, wherein the first and third materials are the same and are a saline solution.

20. The shield of claim 17, wherein the fourth material is a sheet of PVC or UHMWPE.

21. The shield of claim 1, wherein the material comprising each of the first, second and third layers is continuous across an entire surface area within a perimeter of each of the first, second and third layers.

* * * * *